US007596254B2

(12) United States Patent
Liebschner et al.

(10) Patent No.: US 7,596,254 B2
(45) Date of Patent: Sep. 29, 2009

(54) INTRA-OPERATIVE 3-D RECONSTRUCTION OF BONE CEMENT BOLI USING X-RAYS

(75) Inventors: Michael Liebschner, Houston, TX (US); Alistair Templeton, Houston, TX (US)

(73) Assignee: William Marsh Rice University, Houston, TX (US)

(*) Notice: Subject to any disclaimer, the term of this patent is extended or adjusted under 35 U.S.C. 154(b) by 723 days.

(21) Appl. No.: 11/378,744

(22) Filed: Mar. 17, 2006

(65) Prior Publication Data

US 2007/0219445 A1     Sep. 20, 2007

(51) Int. Cl.
*G06K 9/00* (2006.01)
*A61B 6/00* (2006.01)
*A61B 17/58* (2006.01)

(52) U.S. Cl. ............... 382/128; 600/431; 606/92
(58) Field of Classification Search ............ 382/128, 382/129, 130, 131, 132, 133, 134, 154, 285, 382/294; 378/4, 21, 23, 24, 25, 26, 27, 46, 378/92, 101, 140, 901; 600/407, 431, 562, 600/587; 606/74, 92, 94, 105, 280, 281, 606/297, 902, 906, 909; 356/613
See application file for complete search history.

(56) References Cited

U.S. PATENT DOCUMENTS

| | | | | |
|---|---|---|---|---|
| 5,692,507 | A | * | 12/1997 | Seppi et al. ............ 600/407 |
| 5,951,475 | A | * | 9/1999 | Gueziec et al. ........... 600/425 |
| 6,355,255 | B1 | | 3/2002 | Alford et al. |
| 7,522,744 | B2 | * | 4/2009 | Bai et al. ............ 382/100 |

| | | |
|---|---|---|
| 2005/0113691 A1 | 5/2005 | Liebschner |
| 2005/0129726 A1 | 6/2005 | Liebschner |

OTHER PUBLICATIONS

Jin, Yinpeng; Angeline, Elsa; Mangla, Sundeep; Choi, In Sup; Kemkers, Richard; Timmer, Jan; Laine, Andrew; "Multiscale Denoising and Enhancement of 3D Rotational X-ray Imaging for Percutaneous Vertebroplasty"; IEEE FMBS; 2003; 4 pp.; New York, NY USA.

(Continued)

*Primary Examiner*—Abolfazl Tabatabai
(74) *Attorney, Agent, or Firm*—Conley Rose, P.C.; Rodney B. Carroll

(57) ABSTRACT

The present invention provides method of generating a 3-D image of at least one cement bolus in relation to a bone comprising acquiring a plurality of fluoroscopic images of the bolus during or after a bone cement injection procedure. The method further comprises registering each fluoroscopic image with a CT scan image of the bone. Additionally, the method comprises outlining the bolus in each fluoroscopic image to generate a plurality of silhouettes of the bolus. The method also comprises projecting the silhouettes on to the CT scan image to generate a plurality of back-projections. Moreover, the method comprises identifying a plurality of bolus voxels to generate the 3-D image of the bolus, wherein each bolus voxel comprises an intersection of at least two back-projections. Furthermore, a method for intra-operative imaging of at least one bolus of bone cement during a bone cement injection procedure is disclosed.

23 Claims, 9 Drawing Sheets

OTHER PUBLICATIONS

Verlaan, Jorrit-Jan; van de Kraats, Everine B.; Dhert, Wouter JA; Oner, F. Cumhur; "The Role of 3-D Rotational X-ray Imaging in Spinal Trauma"; Department of Orthopedics and Image Processing, University Medical Center Utrecht, 3584CX, Utrecht, The Netherlands; pp. S-B98-S-B103.

van de Kraats, Everine B.; van Walsum, Theo; Verlaan, Jorrit-Jan; Niessen, Wiro J.; "Noninvasive MR to 3D Rotational X-ray Registration of Vertebral Bodies for Image-Guided Spine Surgery;" Spine, vol. 29, No. 3, Chapter 4, pp. 293-287; 2004; USA.

Verlaan, Jorrit-Jan; ven de Kraats, Everine B.; van Walsum, Theo; Dhert, Wouter J.A.; Oner, F. Cumhur; Niessen, Wiro J.; "Three-Dimensional Rotational X-ray Imaging for Spine Surgery"; Spine; 2005; 30 (5): 556-561; Lippincott Williams & Wilkins USA.

van de Kraats, Everine B.; van Walsum, Theo; Verlaan, Jorrit-Jan; Oner, F. Cumhur; Viergever, Max A. Niessen, Wiro J.; "Noninvasive Magnetic Resonance to Three-Dimensional Rotational X-ray Registration of Vertebral Bodies for Images-Guided Spine Surgery"; Spine 29(3): 293-297; Feb. 2004; Lippincott Williams & Wilkins USA.

* cited by examiner

INTRA-OPERATIVE 3-D RECONSTRUCTION OF BONE CEMENT BOLI USING X-RAYS

CROSS-REFERENCE TO RELATED APPLICATIONS

Not applicable.

STATEMENT REGARDING FEDERALLY SPONSORED RESEARCH OR DEVELOPMENT

BACKGROUND

1. Field of the Invention

This invention relates to generally to the field of three-dimensional imaging. More specifically, the invention relates to an intra-operative method of visualizing boli during a bone cement injection procedure.

2. Background of the Invention

Percutaneous bone cement injection procedures such as vertebroplasty are currently some of the least invasive treatments available for bone surgery. For example, in vertebroplasty, an operator simply injects bone cement i.e. poly(methyl methacrylate) (PMMA), using a syringe passing through the skin, through the pedicles and into the anterior vertebral body. The bone cement forms a bolus which hardens to become much stiffer than bone, thus raising the strength of the vertebra. Success of the procedure is typically determined by restoration of vertebral height and removal of pain, which are typically unrelated to the two major types of complications, cement leakage and over-reinforcement of bone. While fluoroscopic x-ray imaging, commonly used intra-operatively, can aid in the avoidance of leakage, in order to avoid over-reinforcement the procedure needs to be optimized such that less cement is required. Currently, exploration of parameters such as bolus location and shape, important steps in optimization, are only explored in the research setting and will remain academic matters until they can easily be cost-effectively observed and controlled in the clinical setting.

Cement volume is the single most important factor in determining the strength and stiffness increase in fractured bone. Generally, the more cement injected, the stronger the reinforcement, but the higher risk of complications. Aside from leakage, it has been found that many patients suffer fractures in adjacent vertebrae at a later date. This side effect may be a result of the higher stiffness of the reinforced vertebra compared to the surrounding vertebrae. The difference in stiffness may cause high stresses in the immediately superior and inferior bones which are often already weakened by a systemic condition such as with osteoporosis. Thus, the amount injected is typically limited, and alternative, less stiff materials have been explored. To further reduce the amount of fill necessary to reinforce a vertebral body, one needs to take into consideration the geometry of the bolus; if stronger reinforcement can be achieved by alternative arrangements of the cement, less total material is necessary. In order to implement such measures, appropriate visualization tools are necessarily, because the operator must make adjustments during the procedure as the specific features of the treated bone influence where the cement flows during injection.

Computed tomography (CT), occasionally performed before the procedure, yields an accurate three-dimensional picture of the bone, and if post-operative, of the bone cement within the bone. However, CT scanners are somewhat expensive to use, take additional time to schedule and perform, and are not always immediately available. Fluoroscopic CT, while an ideal technology for the procedure being real-time and capable of watching for stray channels of cement and calculating the location of the bolus, is quite expensive and less available than CT. Because of the sheer number of vertebroplasty procedures preformed, on-site monitoring of the procedure is thus typically implemented via X-ray fluoroscopy, with which the operator can gain a real-time, two dimensional picture of the current condition inside the bone. This helps to visualize needle position and depth and can identify certain problems such as cement leakage, but does not offer much insight into the three-dimensional positioning and shape of the bolus. Additionally, the two dimensional picture does not provide any information regarding the optimal volume of the bolus.

Consequently, there is a need for a simple, inexpensive, intra-operative method to monitor the 3-D position and shape of a bone cement bolus during a percutaneous bone cement injection procedure.

BRIEF SUMMARY

These and other needs of the art are addressed by method of generating a 3-D image of at least one cement bolus in relation to a bone comprising acquiring a plurality of fluoroscopic images of the cement bolus during or after a cement injection procedure. The method further comprises registering each fluoroscopic image with a CT scan image of the bone. Additionally, the method comprises outlining the bolus in each fluoroscopic image to generate a plurality of silhouettes of the bolus. The method also comprises projecting the silhouettes on to the CT scan image to generate a plurality of back-projections. Moreover, the method comprises identifying a plurality of bolus voxels to generate the 3-D image of the bolus, wherein each bolus voxel comprises an intersection of at least two back-projections.

In another embodiment, these and other needs in the art are addressed in one embodiment by a method for intra-operative imaging of at least one bolus of bone cement during a bone cement injection procedure comprising injecting at least one bolus of bone cement into at least one bone. The method also comprises acquiring a plurality of fluoroscopic images of the bolus at a plurality of angles. In addition, the method comprises registering each fluoroscopic image with a CT scan image of the bone. Moreover, the method comprises tracing the bolus in each fluoroscopic image to generate a plurality of silhouettes of the bolus. Additionally, the method comprises projecting the silhouettes on to the CT scan image. Furthermore, the method comprises identifying a plurality of bolus voxels to generate an on-site three-dimensional image of the bolus, wherein each bolus voxel comprises an intersection of at least two back-projections and optionally, repeating the method based on the on-site three-dimensional image of the bolus.

Because repeated CT scans create extra cost and radiation exposure to the patient and are not immediately available post-treatment, they are typically not used to monitor the results of vertebroplasty, rather as follow-up. The invented process is useful in that it can provide similar information to a second, post-operative CT scan both on-site and less expensively. The process may be used as an evaluation tool for researchers and physicians for estimating the shape of the injected bone cement after a percutaneous bone cement injection procedure, and thus the effectiveness of the procedure. Symmetrical distribution of the bone filler material may be important in preventing secondary damage to the vertebral body. This symmetry may be easily evaluated in an inferior-superior image of the bone. Such information available intra-operatively may prove to be invaluable to a physician.

In research, the method may provide a less expensive method to create finite element models, which when validated may provide invaluable information about the efficacy of the procedure, with modifications. The same process may naturally be used to monitor the injection of other materials as replacements of PMMA are explored. It may also be used to judge the size and shape of bone defects, either naturally or pathologically occurring. The method is not aimed at replacing CT scans where they are required, only at supplementing 3-D imaging where CT scans are impractical. In addition, this technique may prove useful in imaging bone damage, tumors, and other disease in a three-dimensional model during operative procedures. Updating developed 3-D models intra-operatively has been a long felt need for physicians working with surgical stereotactic navigation systems in tumor resection. For non-medical applications, the technique may be used for approximating non-symmetrical shapes hidden behind an enclosure.

The process is based upon limited-projection reconstructions, where the number of projections is too few for rigorous tomographic calculations. The primary difference is that this process caters to a particular situation in which we are reconstructing the geometry of one object within another, with no regard to the shape of the larger object. This simplifies the math, and allows integration into the procedure without major changes to the current process. Furthermore, the present invention applies to bone cement injection procedures in an intra-operative setting. Such imaging modalities could potentially improve clinical outcome of the patients. The advantages of the present invention can be obtained without adding additional time to the operation.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ".

"Bone cement" means any injectable material that hardens to form a bone fixative.

"Bolus" means a mass of bone cement.

"Image registration" means the placement or re-orientation of two images in such a manner as to align them with each other.

"Percutaneous bone cement injection" means any minimally invasive procedure where bone cement is injected into bone through the skin.

"Voxel" means a unit of volume corresponding to the smallest element depicted in a three-dimensional computed tomography (CT) image. In other words, the three-dimensional equivalent of a pixel.

DETAILED DESCRIPTION OF THE PREFERRED EMBODIMENTS

Figure 1:
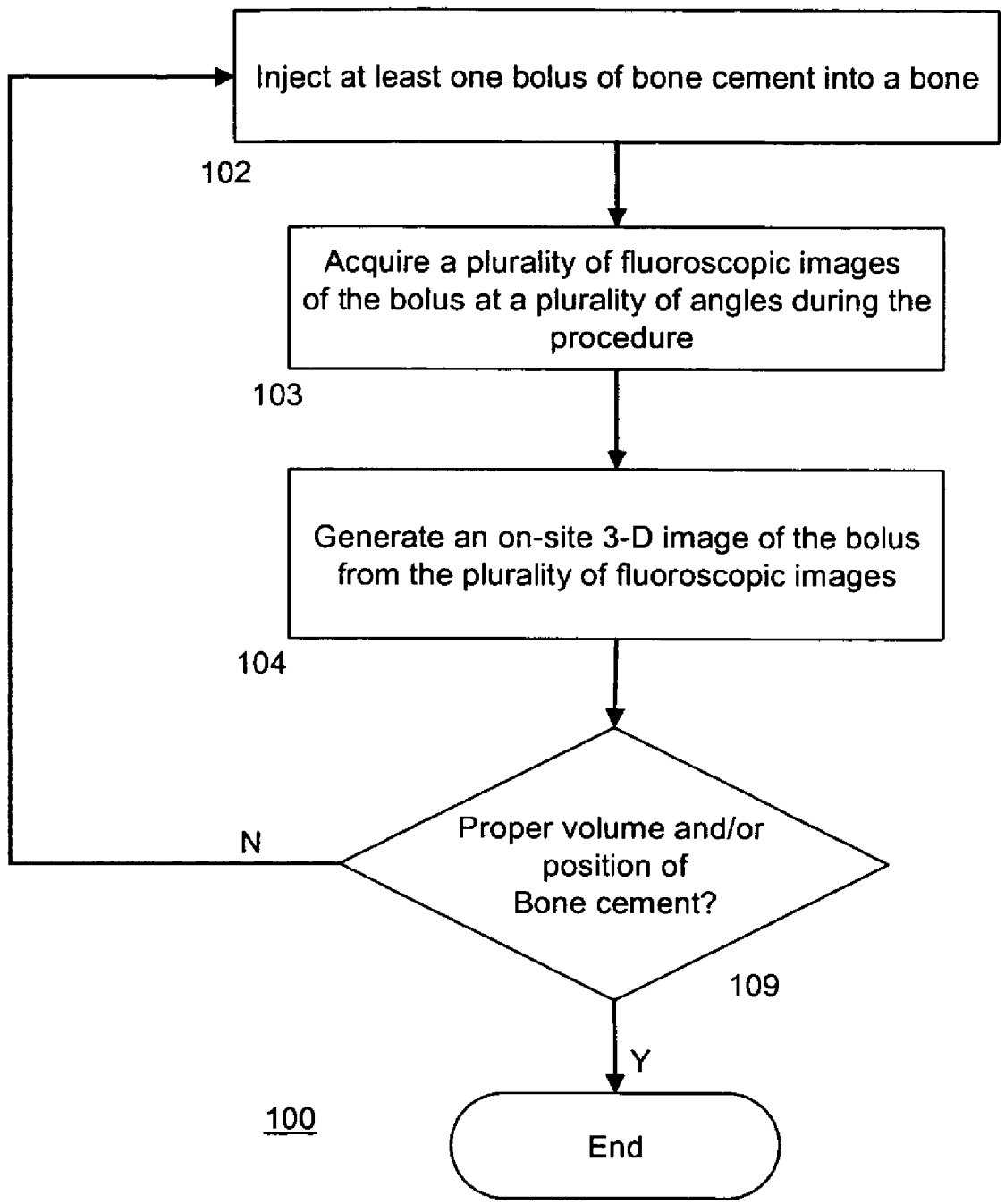
FIG. 1 a flow diagram representing an embodiment of a method for intra-operative imaging of at least one bolus of bone cement during a bone cement injection procedure.

FIG. 1 illustrates a flow diagram of a method 100 for intra-operative imaging of a bolus of bone cement during a bone cement injection procedure. The method 100 may initially comprise the step 102 of injecting a bolus of bone cement into a bone. In an embodiment of the invention, the patient's spine and surrounding tissue may be constantly monitored through fluoroscopic imaging at step 103 by acquiring a plurality of fluoroscopic images at a plurality of angles during the bone cement injection procedure. In preferred embodiments, the bone cement injection procedure may comprise vertebroplasty or kyphoplasty where the bone cement is injected into the vertebra. However, it is envisioned that the method may be used with bone cement injection procedures involving any bone in the body.

Step 103 may further comprise acquiring fluoroscopic images while inserting a needle through the skin into the bone to guide the surgeon. During the bone cement injection, step 103 may comprise acquiring additional fluoroscopic images to stop injection at the onset of bone cement leakage out of the bone. In another embodiment, step 103 may comprise taking fluoroscopic images after injection of the bone cement.

The orientation of the imaging system may generally be in the anterior-posterior (AP) and medial lateral (ML) directions. In typical embodiments, the step 103 may include taking fluoroscopic images of one or more angles of a bone during a percutaneous bone cement injection procedure. The images may be taken at any angle ranging from 0° to 270°, preferably ranging from 0° to 180°. Additionally, the images may be taken at any suitable angular increments. In an embodiment, the images may be taken at 15° increments. Alternatively, the angular increments may be unequally spaced. For example, 6 images may be taken at angular increments at 15°, whereas the next 6 images may be taken at angular increments of 10°. Preferably, the image may be taken from the postero-lateral angle on one side to the postero-lateral angle on the opposite side of a patient or vice-versa.

In some embodiments, no more than 3 images may be needed for approximating the bone filler shape inside the vertebral body, alternatively no more than 7 images may be taken, alternatively no more than 12 images may be taken. Preferably, less than 50 images may be taken during the process. In further embodiments, a plurality of boli may be imaged. Alternatively, the plurality of boli may be located in different bones.

In preferred embodiments, the images acquired in step 103 may be taken by an X-ray imaging device. However, any device capable of imaging a bone may be used. The imaging device may be completely automated such that the device automatically takes the desired number of images at the appropriate angles. In certain embodiments, a user may enter the desired number of images or the desired angular increments in to the device. Also, in additional embodiments, step 103 may comprise using X-ray imaging, digital X-rays, intraoperative CT, open MRI, or ultrasound to acquire the images. One example of a commercially available device is a C-arm 3-D rotational x-ray device. The images may be stored as a digital image in any suitable format such as BMP, JPEG, MPEG, GIF, TIFF, PNG, WMF, or PCX. Generally, the images may be stored on a digital workstation or a computer.

To aid the identification of the bone cement-bone interface, a contrast agent may be mixed into the bone cement during preparation. Examples of suitable contrast agents include without limitation, barium sulfate, iodine based contrast agents, ionic contrast agents, nonionic contrast agents, or combinations thereof. The effect of the contrast agent on the mechanical properties of the bone cement is negligible. The imaging process may be used with any type of bone cement material. Although PMMA is the primary material used as bone cement, the bone cement may comprise other materials such as poly(propylene fumarate), calcium phosphate, calcium carbonate, biodegradable polymers, hydroxyapatite, ceramics, antibiotics, or combinations thereof. Thus, any type of bone cement may be imaged using the disclosed process.

Generally, a CT scan and the plurality of fluoroscopic images may be used to reconstruct the 3-D image of the bolus. The CT scan may comprise a pre-operative scan taken of the patient's own bone prior to step 102. Any suitable clinical CT scanner may be used. In certain embodiments, 1 mm transverse slices of the surgical site may be scanned. Alternatively, the CT scan may be a stock image of a bone taken from another patient. Typically, the CT scan image comprises an image of a vertebra.

Figure 2:
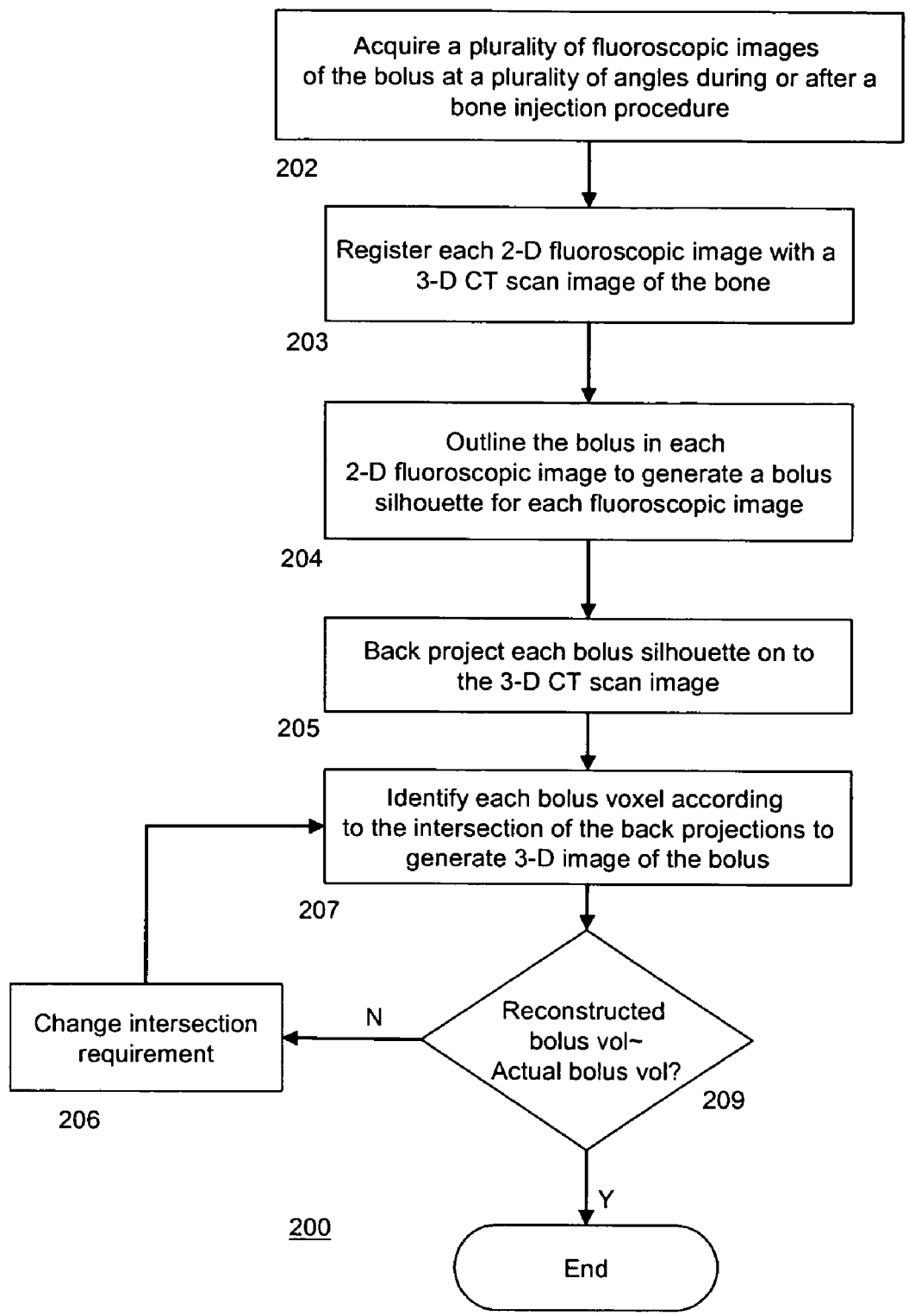
FIG. 2 is a flow diagram representing an embodiment of a method for reconstructing a 3-D image of a bolus within a bone.

FIG. 2 illustrates a flow chart of the 3-D image reconstruction method 200 which in some embodiments may occur at step 104 of method 100. The method 200 is preferably completely automated through software or a computer. However, in some embodiments, one or more of the steps may be manually executed. The method 200 may initially comprise a step 202 where a plurality of fluoroscopic 2-D images of the bolus may be acquired at a plurality of angles as described in detail above.

Figure 4:
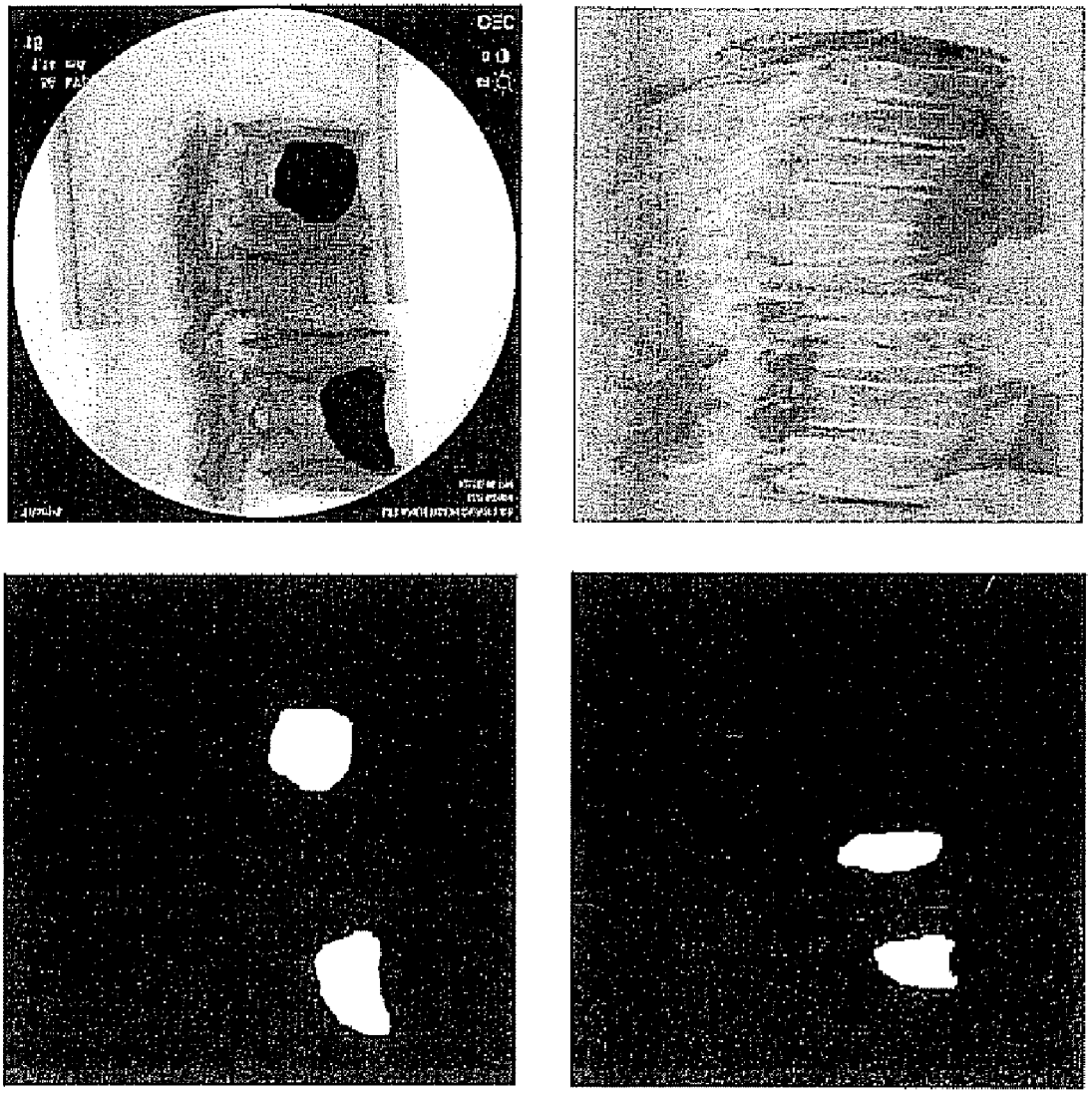
FIG. 4 illustrates transformation from PMMA read on fluoroscopic image to match the CT scan. Corresponding features on the radiograph (top left) and CT projection (top right; produced by mathematically summing the pixel values of the volume in the given direction, a.k.a. a radon transform) were identified, creating a map for moving from one to the other. The PMMA was then isolated from the radiograph (bottom left) and transformed into the CT domain (bottom right)

The image reconstruction method 200 may further comprise an image registration step 203. In order to visualize the bone cement in the frame of a CT scan, the images may be transformed such that the location of a pixel on the fluoroscopic image has a meaning in the 3-D CT space. In a vertebroplasty embodiment, the CT scan of vertebrae may be separated into individual spinal segments. Simulated projections may then be used to create pre-operative radiographs by summing the density along straight lines through the volume in each CT image. Preferably, the simulated projections are at matching angles to the fluoroscopic images. Thus, for each projection angle of a given bone, a simulated projection may be used to depict the pre-operative state and a fluoroscopic radiograph may be used to depict the postoperative state. The two corresponding images have different resolutions and positions, and thus the process may generally comprise an image registration or alignment step 203. To register each fluoroscopic image with the corresponding simulated projection, the image registration step 203 may comprise identifying a quadrilateral bounded by four features (points) of the spinal segment on each image and may additionally comprise translating, rotating and resealing the fluoroscopic image to match the simulated projection resolution and position (See FIG. 4).

Figure 3:
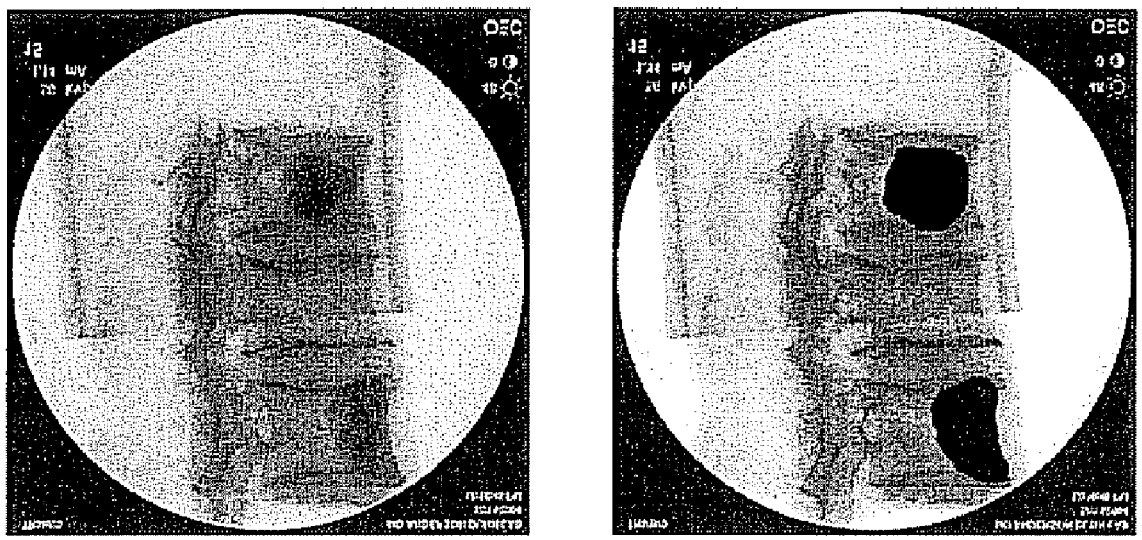
FIG. 3 shows fluoroscopic images of a spinal segment. The outlines of the PMMA were traced in the original (left), and labeled for easy identification as depicted on the right.

Once the image registration step 203 is performed, the bone cement bolus may be isolated in each image, creating a silhouette of the bolus at each projection angle as described in step 204. Each radiograph may be processed using a commercial image analysis software package such as Analyze (AnalyzeDirect, Lenexa Kans.) to identify the bolus. The 2-D outline of the bolus may be traced on each image (FIG. 3). In typical embodiments, a combination of thresholding and manual outlining may be used to trace the bolus in the image. In other embodiments, the tracing may be completely automated through use of advanced image processing techniques or algorithms. Each pixel within the outline may be tagged to form a silhouette of the bolus. Once formed, each of the silhouettes may be back-projected across the three-dimensional space of the CT scan as seen in step 205, creating an extrusion of each shape.

Figure 5:
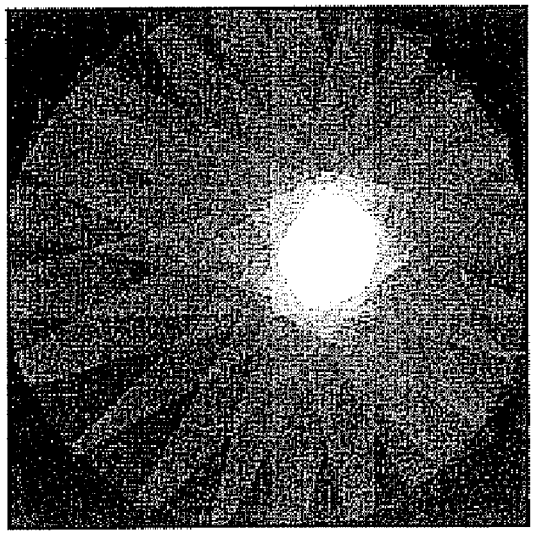
FIG. 5 illustrates a slice of a resulting back-projected PMMA volume. On the left, all 12 back-projections are overlaid, and the brightest central shape is the full intersection. The right represents the area where 10 or more of the back-projections intersect, which most accurately predicts the PMMA volume.
Figure 5:
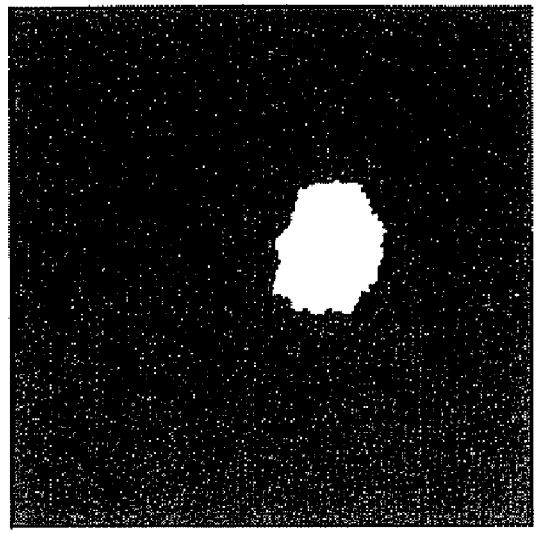

The voxels which represent the bone cement may be identified in the three-dimensional space by identifying the intersection of the back-projections (See FIG. 5) in step 207. In general, the voxels in which all the projections intersect may be taken as the bone cement volume. Thus, if there are 12 projections, a voxel where all 12 projections intersect may be designated as a bone cement voxel. However, in some embodiments, the voxels in which less than all the projections intersect may also be counted as a bolus voxel. In order to test the accuracy of the reconstruction, the volume of the reconstructed bolus may be compared in step 209 to the amount of cement injected during the procedure, a known quantity. If the reconstructed volume is less than the actual amount of bone cement injected, the number of intersecting projections required in order to be designated as a bolus voxel may be reduced in step 206. By way of example only, for an embodiment with 12 projections, instead of requiring a voxel in which all 12 projections intersect, only 11 projections may be required. The volume may then be recalculated. In preferred embodiments, the number of intersecting projections that provides the most accurate volume reconstruction is used.

Step 207 may comprise exporting the identified bolus voxels to MATLAB® (Mathworks, Nattick Mass.) or other data analysis software for re-construction of the bolus image. In some embodiments, an algebraic reconstruction algorithm (ART) may be implemented to reconstruct the image. The reconstructed boli may be overlaid onto the original CT scans and transferred back to commercial image analysis software for further analysis. The resulting image provides three-dimensional visualization of the bolus and its position within the bone.

The results may be presented either on the fluoroscope screen or a separate display. If the treatment results are satisfactory, the physician may finish the procedure. Referring back to FIG. 1, the surgeon may optionally choose to inject more bone cement at the same or different anatomical regions if the volume and/or position of the bone cement is not optimal in step 109. In further embodiments, the CT scan and the acquired shape of the bone cement bolus may be used to construct finite element models to estimate the bone strength. The finite element models may be coupled to the visualization process to provide biomechanical feedback in addition to image feedback to an operator.

The number of projections used may vary according to the efficacy of the process. Though part of the attraction of the process is the simplicity of the algorithm, there are more sophisticated limited-projection reconstruction methods that may be employed. In addition to using this procedure for bone cement injection procedures, it is envisioned that the process may be used for other medical applications in need for intraoperative imaging such as tumor resection, healing monitoring, implant fixation, etc. To further illustrate various illustrative embodiments of the present invention, the following example is provided.

EXAMPLE

Six cadaveric spinal segments (T9-L4; Male, ages 63-88) from a coinciding study were analyzed. They were placed two at a time in a water bath and scanned in a clinical CT scanner with 1 mm transverse slices. Each specimen was then prepared by cutting off the L1-L3 segment and removing the intervertebral discs from each end. Vertebroplasty was then performed on each of the six 3-level segments; every L1 and L3 vertebra was then injected with 10 cc of PMMA, in a bi-pedicular injection scheme (two discrete injections, one through each lateral pedicle).

After treatment, each specimen was transferred to a cylindrical container with a stand and demarcated angles. The container was placed on a treatment table, and a fluoroscope projector was placed directly above in a fixed position. By rotating the container in fixed increments, 12 fluoroscopic X-ray images were taken evenly spaced angles of 15° over a 180° range, as opposite projections provide similar information. Each X-ray was saved as a digital image (bitmap) and transferred to the analysis computer, an SGI Octane2 with dual 400 MHz processors. In a separate study, each specimen was potted in PMMA, had the pedicles removed, and was mechanically tested to fracture after which further CT scans were taken. We were provided with these data to evaluate our results as a visual benchmark. In each segment the central bone of the 3-vertebra segment fractured but the PMMA-reinforced bones remained largely intact, allowing such a comparison to be made.

Image Analysis

Figure 6:
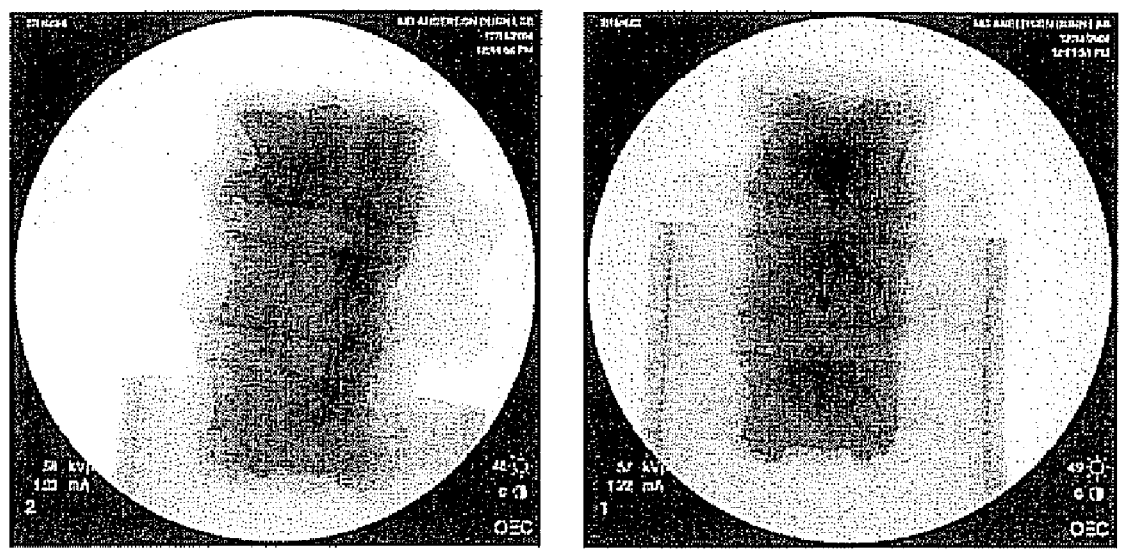
FIG. 6 illustrates the challenges in identifying PMMA. On some fluoroscopic images it was difficult to accurate discern the contribution of PMMA to the image from that of the posterior elements, and surrounding bone.

The outline of the bolus on the fluoroscopic X-rays was, on some of the images, very difficult to identify (FIG. 6). This was due to several reasons: 1) On all images, at the periphery of the PMMA on each image (where a given ray from the fluoroscope travels through a small amount of bone cement), there was very little contrast to the bone. 2) In some projections, the posterior elements (consisting of generally denser bone) overlap the anterior vertebral body, the area of interest, and were difficult to distinguish from the PMMA. 3) In some specimens, the contrast between the PMMA and the bone was generally low. The registration of the images proved more consistent. The chosen features were consistently identified, typically the corners of the vertebral bodies in each projection, to within a few pixels.

Image Reconstruction

Boli consistent with the PMMA outlines identified in the fluoroscopic images were successfully generated. The number of intersecting projections required to achieve the correct PMMA volume varied between specimens (See Table 1).

| Specimen number | Vol. @ 12 proj. | Vol. @ 11 proj. | CT-Based Volume Calculations | % Error 12 projections | % Error CT images |
|---|---|---|---|---|---|
| 1 | 19.2 cc | 24.9 cc | 22.4 | −4.00 | −12.00 |
| 2 | 18.9 cc | 25.1 cc | 22.9 | −5.50 | 14.5 |
| 3 | 16.8 cc | 21.0 cc | 15.7 | −16.00 | −21.50 |
| 4 | 17.2 cc | 20.8 cc | N/A | 14.0 | N/A |
| 5 | 20.1 cc | 26.3 cc | 23.0 | 0.5 | 15.00 |
| 6 | 21.6 cc | 26.2 cc | 23.9 | 8.00 | 19.50 |

This is attributed to inconsistency in the bone cement contrast, making the tracing of the bolus on the fluoroscopic images more accurate on some images than others. On four of the six spines analyzed, all 12 projections intersected to create boli of the appropriate size, while on the other specimens 11 of 12 were necessary.

Figure 7:
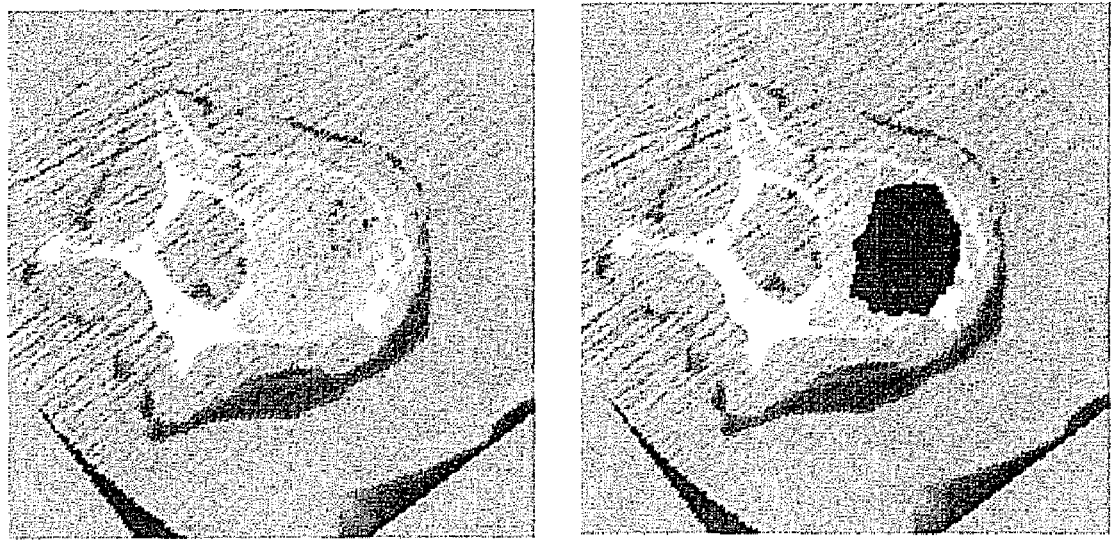
FIG. 7 shows an original CT scan (left) and simulated post-operative scan (right). On a transverse slice of the CT volume, the PMMA is represented in black within the vertebral body. The streaks through the image are artifacts resulting from rotating the image for simple angle identification.
Figure 8:
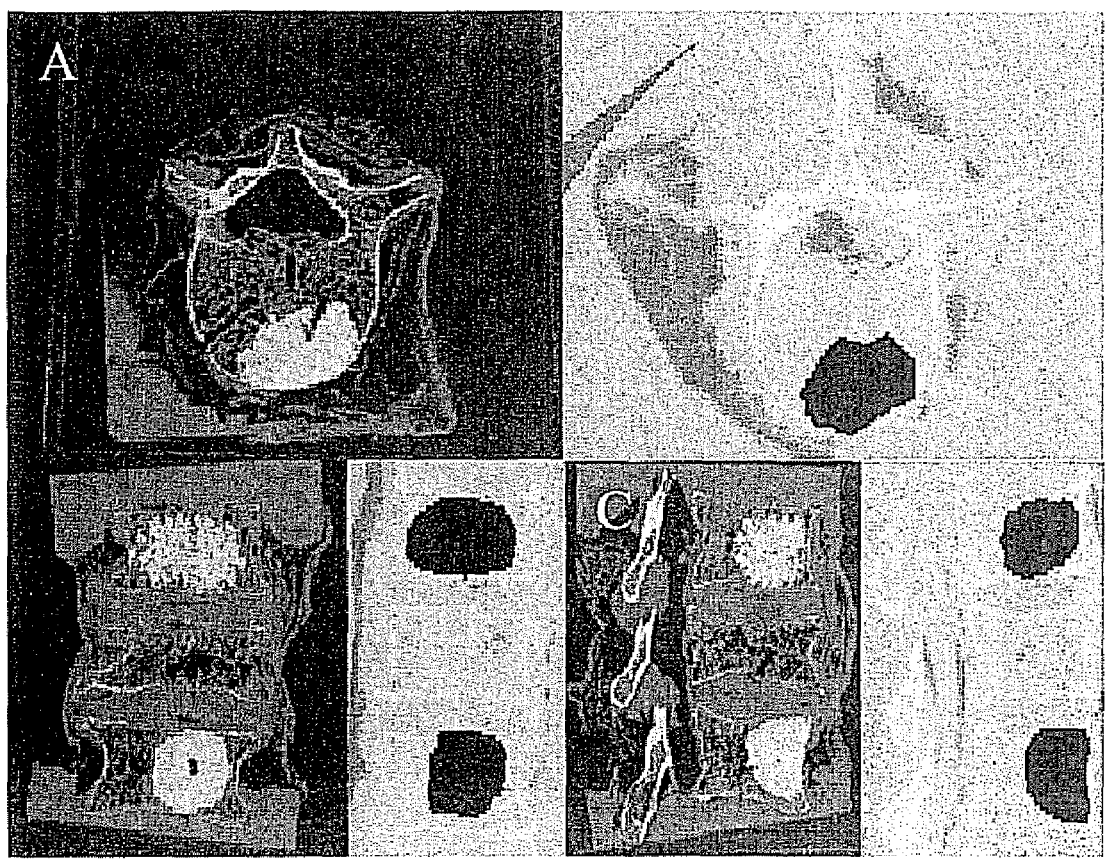
FIG. 8 shows post-operative CT scans with reconstructed CT scans. Images with black backgrounds are representative slices of a CT scan taken after injection from the (a) axial, (b) coronal, and (c) sagittal views. Adjacent to the right of each, with gray backgrounds, are slices taken as close as possible, of the same vertebra. Note that the post-operative CT scan underwent a compression-fracture experiment in a separate study, resulting in some changes in bone features.
Figure 9:
FIG. 9 shows three-dimensional visualization of PMMA bolus within a single vertebra.

By registering the pre-operative CT scan to the digital radiographs and overlaying the bolus position we were able to show the location of the PMMA within each slice of the CT scan (FIG. 7) for visual inspection and comparison to post-operative CT scans (FIG. 8). Some image artifacts were produced during rotation of the images, but they do not interfere with estimation of bolus location or size. The fully reconstructed three-dimensional bolus within the vertebra is shown in FIG. 9. By using the pre-operative CT scan and reconstructing the PMMA using fluoroscopic images, it is possible to estimate the location of the bone cement within the bone, for possible intra- and post-operative evaluation.

Although the present invention and its advantages have been described in detail, it should be understood that various changes, substitutions and alterations may be made herein without departing from the spirit and scope of the invention as defined by the appended claims.

What is claimed is:

1. A method of generating a 3-D image of at least one cement bolus in relation to a bone comprising:
   a) acquiring a plurality of fluoroscopic images of the cement bolus during or after a cement injection procedure;

b) registering each fluoroscopic image with a CT scan image of the bone;
c) outlining the bolus in each fluoroscopic image to generate a plurality of silhouettes of the bolus;
d) projecting the silhouettes on to the CT scan image to generate a plurality of back-projections; and
e) identifying a plurality of bolus voxels to generate the 3-D image of the bolus, wherein each bolus voxel comprises an intersection of at least two back-projections.

2. The method of claim 1 wherein step b) further comprises acquiring the plurality of fluoroscopic images of the bolus using a C-arm X-ray device.

3. The method of claim 1 wherein step b) comprises acquiring the plurality of fluoroscopic images at evenly spaced angles.

4. The method of claim 1 wherein step b) comprises acquiring the plurality of fluoroscopic images at unevenly spaced angles.

5. The method of claim 1 wherein step b) comprises acquiring the plurality of fluoroscopic image at 15° angular increments.

6. The method of claim 1 wherein step c) comprises a combination of thresholding and manual outlining.

7. The method of claim 1 wherein steps b)-e) are completely automated.

8. The method of claim 1 wherein each bolus voxel comprises the intersection of all the back-projections.

9. The method of claim 1 wherein each bolus voxel comprises the intersection of less than all the back-projections.

10. The method of claim 1 wherein step e) further comprises applying an algebraic reconstruction algorithm to reconstruct the 3-D image.

11. The method of claim 1 wherein the bone cement injection procedure comprises vertebroplasty or kyphoplasty.

12. The method of claim 1 wherein the plurality of fluoroscopic images comprises no more than 12 images.

13. The method according to claim 1 wherein the CT scan image comprises a pre-operative CT image of the bone.

14. The method of claim 1 wherein the CT scan image comprises a stock CT image of the bone.

15. The method of claim 1 further comprising repeating steps a)-d) for a plurality of boli.

16. A method for intra-operative imaging of at least one bolus of bone cement during a bone cement injection procedure comprising:
a) injecting at least one bolus of bone cement into at least one bone;
b) acquiring a plurality of fluoroscopic images of the bolus at a plurality of angles;
c) registering each fluoroscopic image with a CT scan image of the bone;
d) tracing the bolus in each fluoroscopic image to generate a plurality of silhouettes of the bolus;
e) projecting the silhouettes on to the CT scan image to form a plurality of back-projections;
f) identifying a plurality of bolus voxels to generate an on-site three-dimensional image of the bolus, wherein each bolus voxel comprises an intersection of at least two back-projections; and
g) optionally, repeating steps a)-c) based on the three-dimensional image of the bolus.

17. The method of claim 16, further comprising mixing an amount of contrast agent in the bone cement sufficient to allow it to be visualized.

18. The method of claim 17 wherein the contrast agent comprises barium sulfate, an iodine-based contrast agent, an ionic contrast agent, a nonionic contrast agent, or combinations thereof.

19. The method of claim 16 wherein the bone cement comprises PMMA, calcium phosphate, poly(propylene fumarate), hydroxyapatite, ceramics, biodegradable polymers, or combinations thereof.

20. The method of claim 16 wherein step b) is performed during or after step a).

21. The method according to claim 16, further comprising taking a pre-operative CT scan of the bone to generate the CT scan image prior to step a).

22. The method of claim 16 wherein step c) is carried out on a computer.

23. The method of claim 16 further comprising performing finite element analysis on the three-dimensional image of the bolus.

* * * * *

UNITED STATES PATENT AND TRADEMARK OFFICE
CERTIFICATE OF CORRECTION

PATENT NO. : 7,596,254 B2  Page 1 of 1
APPLICATION NO. : 11/378744
DATED : September 29, 2009
INVENTOR(S) : Liebschner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 853 days.

Signed and Sealed this

Fourteenth Day of December, 2010

David J. Kappos
*Director of the United States Patent and Trademark Office*